United States Patent [19]
Ohi

[11] Patent Number: 5,248,822
[45] Date of Patent: Sep. 28, 1993

[54] DISULFIDE COMPOUND

[75] Inventor: Hideo Ohi, Shizuoka, Japan

[73] Assignee: Ihara Chemical Industry Co., Ltd., Tokyo, Japan

[21] Appl. No.: 920,466

[22] PCT Filed: Dec. 26, 1991

[86] PCT No.: PCT/JP91/01773

§ 371 Date: Aug. 25, 1992

§ 102(e) Date: Aug. 25, 1992

[87] PCT Pub. No.: WO92/12127

PCT Pub. Date: Jul. 23, 1992

[30] Foreign Application Priority Data

Dec. 27, 1990 [JP] Japan .................................. 2-416785

[51] Int. Cl.$^5$ ............................................ C07C 233/07
[52] U.S. Cl. ............................................ 564/154; 564/155
[58] Field of Search ................... 564/154, 155; 568/25

[56] References Cited

U.S. PATENT DOCUMENTS 4,613,675 9/1986 Lee ........................................ 558/170

FOREIGN PATENT DOCUMENTS 60-172958 9/1985 Japan .
62-33148 2/1987 Japan .
2-221254 9/1990 Japan .

*Primary Examiner*—Glennon H. Hollrah
*Assistant Examiner*—Deborah Lambkin
*Attorney, Agent, or Firm*—Oblon, Spivak, McClelland, Maier & Neustadt

[57] ABSTRACT

A novel disulfide compound is presented which can be readily led to 5-amino-2-chloro-4-fluoro-thiophenol in good yield.

A bis-(5-acetamino-2-chloro-4-fluorobenzene)disulfide compound represented by the formula (1):

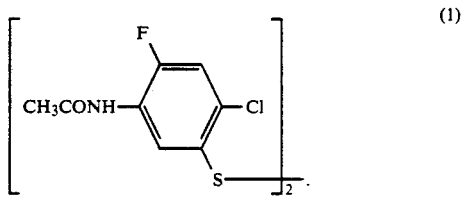

1 Claim, No Drawings

DISULFIDE COMPOUND

TECHNICAL FIELD

The present invention provides bis-(5-acetamino-2-chloro-4-fluorobenzene)disulfide which is useful as an intermediate material for a thiadiazabicyclononane-type agricultural chemical such as a herbicide.

BACKGROUND ART

As a thiadiazabicyclononate-type agricultural chemical, a compound which has a structure of the following formula:

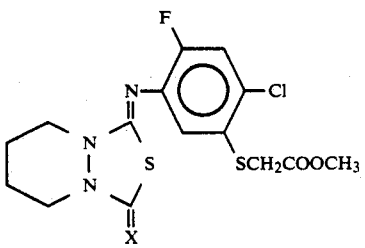
(2)

and which is used as an active substance for a herbicide, is, for example, known (see Japanese Unexamined Patent Publication No. 264489/1988). The compound of this formula (2) (hereinafter represented also as the compound (2), the same applies to other compounds) is produced by using 5-amino-2-chloro-4-fluoro-thiophenol represented by the formula (3) (see U.S. Pat. No. 4,613,675) as the starting material:

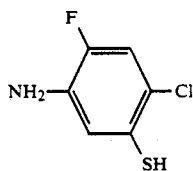
(3)

Heretofore, as a method for obtaining the above compound (3), the following method is known which is a combination of the methods disclosed in Japanese Unexamined Patent Publications No. 172958/1985 and No. 33148/1987:

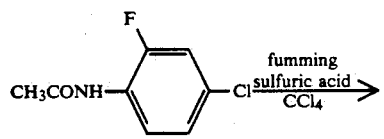

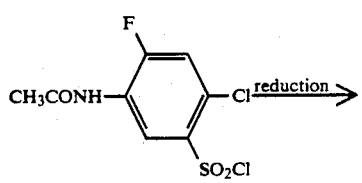

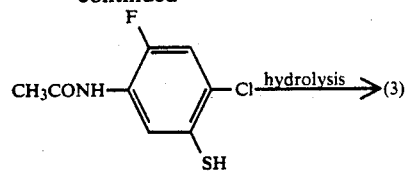

However, the above conventional method had problems with respect to the safety and toxicity, etc. such that it was necessary to use fumming sulfuric acid containing 60% of $SO_3$ which was not easy to use for industrial operation, and besides, phosgene was generated during the reaction using carbon tetrachloride as a solvent. Further, for the reduction of the chlorosulfonyl group, a large amount of a reducing agent as well as an excess amount of an acid was required to be used. Therefore, such a method was not satisfactory as an industrial method.

On the other hand, as a method for obtaining the above compound (3), the following method is also known involving a disulfide compound as an intermediate (see Unexamined Patent Publication No. 221254/1990).

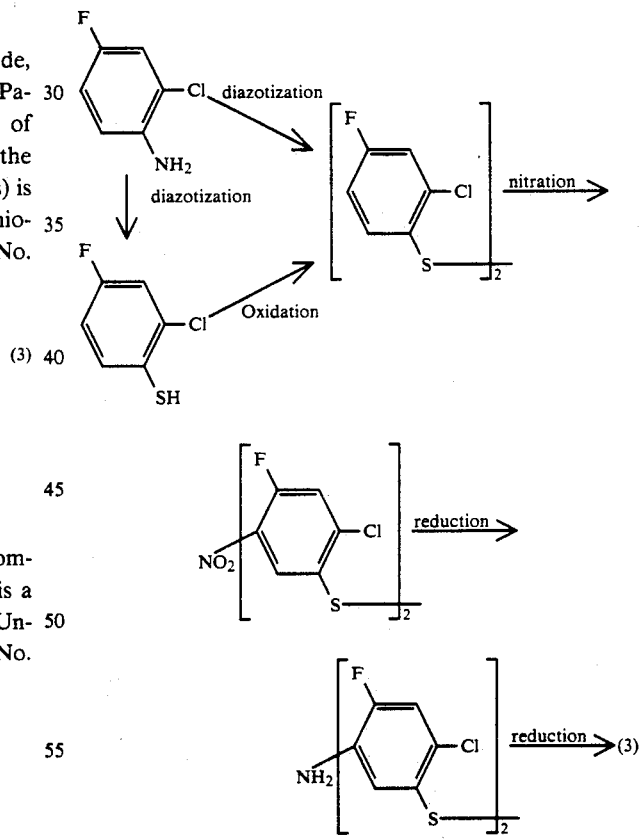

However, in the above method, the diazotization operation is cumbersome. Besides, the yield is low, a side reaction proceeds mainly in the nitration, and the yield is also low. Thus, using the disulfide compound as an intermediate does not provide good results, and this method can not necessarily be regarded as a good method.

The present invention has been made for a purpose of overcoming the above mentioned difficulties of the prior art and to provide a novel disulfide compound which can readily be led to the 5-amino-2-chloro-4-fluoro-thiophenol of the above formula (3) in good yield.

DISCLOSURE OF THE INVENTION

In order to accomplish the above object, the present invention provides a bis-(5-acetoamino-2-chloro-4-fluorobenzene)disulfide compound represented by the formula (1):

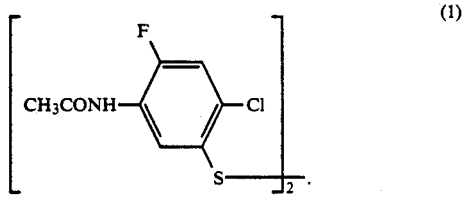

Now, with reference to the following reaction formula, the bis-(5-acetamino-2-chloro-4-fluorobenzene)-disulfide compound of the present invention represented by the formula (1) and a method for leading the disulfide compound (1) to the above mentioned 5-amino-2-chloro-4-fluoro-thiophenol (3), will be described.

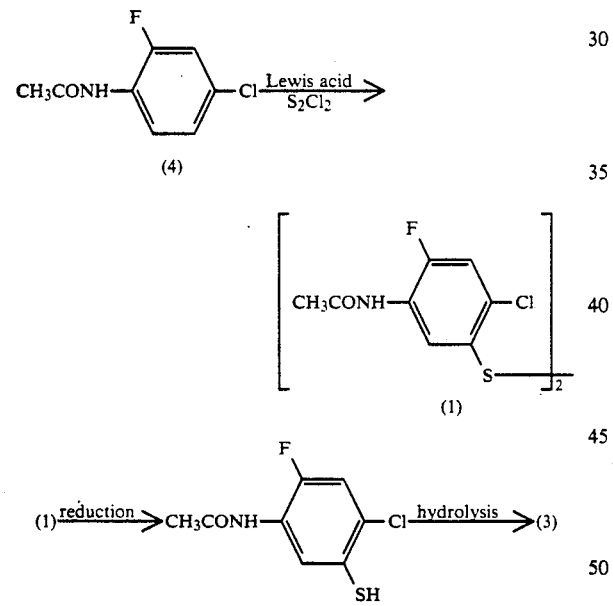

Namely, as the operation to obtain bis-(5-acetamino-2-chloro-4-fluorobenzene)disulfide (1) as the disulfide compound of the present invention, 4-chloro-2-fluoroacetanilide (4) and sulfur monochloride are reacted in the presence of a Lewis acid at a temperature of from 0° to 100° C., preferably from 20° to 50° C.

The Lewis acid to be used in the above operation, may, for example, be aluminum chloride, iron chloride or zinc chloride. Among them, aluminum chloride is preferably used to attain a good yield.

Further, as a solvent, it is possible to use a solvent inert to the reaction to smoothly conduct the reaction. As such a solvent, an organic solvent such as a halogenated hydrocarbon, may, for example, be preferred, and dichloromethane, chloroform or dichloroethane may be used.

The amount of sulfur monochloride to be used in the above operation, is 0.5 mol or more, preferably from 0.6 to 2.5 mols, per mol of the compound (4). Further, the amount of the Lewis acid is from 1 to 5 mols, preferably from 2 to 2.5 mols, per mol of the compound (4). On the other hand, when an organic solvent is used, it may be at least an amount where stirring can be conducted.

Further, the 4-chloro-2-fluoroacetanilide (4) to be used as the starting material can easily be obtained by a method of acylating an aniline as disclosed in Japanese Unexamined Patent Publication No. 51521/1976.

The disulfide compound (1) of the present invention thus obtained can be led to 5-amino-2-chloro-4-fluoro-thiophenol (3) by reducing it with zinc metal in acetic acid, followed by hydrolysis with an aqueous alkaline solution.

Further, the above 5-amino-2-chloro-4-fluoro-thiophenol (3) can be led to an active compound of a thiadiazabicyclononane-type herbicide disclosed in Japanese Unexamined Patent Publication No. 264489/1988, as shown below:

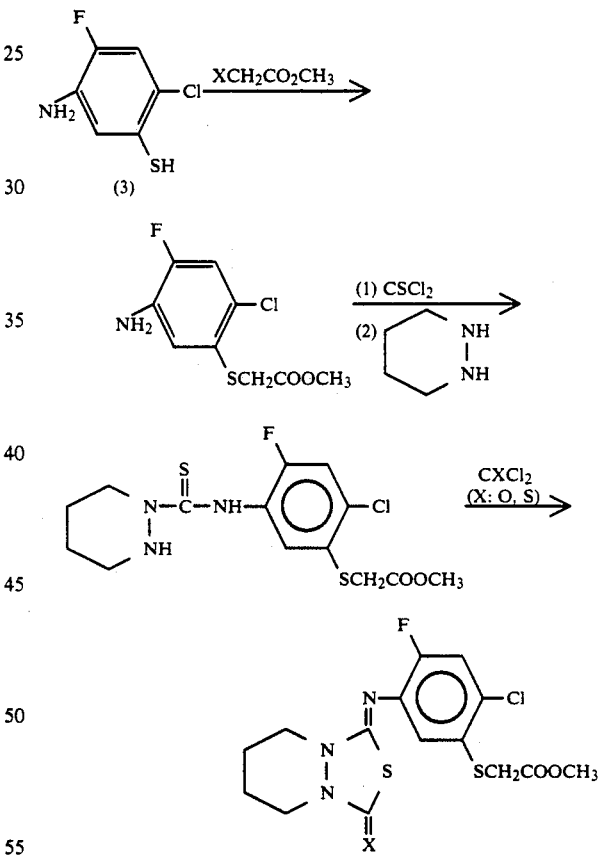

The present invention provides novel bis-(5-acetamino-2-chloro-4-fluorobezene)disulfide (1) by reacting 4-chloro-2-fluoroacetanilide (4) and sulfur monochloride in the presence of a Lewis acid. Further, as shown in the following Reference Example, the disulfide compound (1) of the present invention can be converted to 5-amino-2-chloro-4-fluoro-thiophenol (3) by reduction and hydrolysis.

Accordingly, the present invention can be an intermediate useful for a thiadiazabicyclononane-type compound having herbicidal activities as disclosed in Japanese Unexamined Patent Publication No. 264489/1988.

BEST MODE FOR CARRYING OUT THE INVENTION

Now, the present invention will be described specifically with reference to Examples and Reference Examples.

EXAMPLE 1

Preparation of bis-(5-acetamino-2-chloro-4-fluorobenzene)disulfide

In a 100 ml reaction flask equipped with a condenser, a thermometer and a stirrer, 7.5 g (0.04 mol) of 4-chloro-2-fluoro-acetanilide was suspended in 40 cc of dichloromethane, and 10.7 g (0.08 mol) of anhydrous aluminum chloride was added thereto. The mixture was stirred at room temperature for 30 minutes, and then 4.1 g (0.03 mol) of sulfur monochloride was dropwise added thereto from a dropping funnel. After completion of the dropwise addition, the mixture was reacted at 40° C. for 3 hours. Then, the reaction solution was cooled to room temperature and poured into 200 g of ice water. The organic layer was extracted with 150 ml of ethyl acetate and dried. Then, dichloromethane and ethyl acetate as the solvents were distilled off under reduced pressure, and the residue was washed with a small amount of ethyl acetate to obtain 7.4 g of bis-(5-acetamino-2-chloro-4-fluorobenzene)disulfide (1). Yield was 84.7%. The physical properties and confirmation data are shown below.

Physical property: melting point of 241°–3° C.
Confirmation data
1H-NMR[SO(CD$_3$)]: 9.8(2H,s), 7.39–8.49(4H,q), 2.10(6H,s) MS: Peaks attributable to chlorine isotope were found at P+2 and P+4 based on 436(P).

EXAMPLE 2

Preparation of bis-(5-acetamino-2-chloro-4-fluorobenzene)disulfide

In a 100 ml reaction flask equipped with a condenser, a thermometer and a stirrer, 7.5 g (0.04 mol) of 4-chloro-2-fluoro-acetanilide was suspended in 40 cc of dichloromethane, and 10.7 g (0.08 mol) of anhydrous aluminum chloride was added thereto. The mixture was stirred at room temperature for 30 minutes, and then 8.1 g (0.06 mol) of sulfur monochloride was dropwise added thereto by a dropping funnel. After the completion of the dropwise addition, the mixture was reacted at 40° C. for 3 hours. Then, the reaction solution was cooled to room temperature and poured into 200 g of ice water. The organic layer was extracted with 150 ml of ethyl acetate and dried. Then, dichloromethane and ethyl acetate as the solvents were distilled off under reduced pressure, and the residue was washed with a small amount of ethyl acetate to obtain 6.9 g of bis-(5-acetamino-2-chloro-4-fluorobenzene)disulfide (1). Yield was 79.3%.

REFERENCE EXAMPLE 1

Preparation of 5-acetamino-2-chloro-4-fluorothiophenol

In a 200 ml reaction flask, 6.4 g (0.0146 mol) of bis-(5-acetamino-2-chloro-4-fluorobenzene)disulfide and 9.8 g (0.149 mol) of zinc were suspended in 100 cc of acetic acid and reacted for 6 hours under reflux. After cooling to room temperature, inorganic substances were filtered, and acetic acid was distilled off under reduced pressure, whereby 4.8 g of 5-acetamino-2-chloro-4-fluoro-thiophenol was obtained as white crystals having a melting point of 142.5°–144° C. Yield was 73.1%.

REFERENCE EXAMPLE 2

Preparation of 5-amino-2-chloro-4-fluoro-thiophenol

Into a 100 ml reaction flask, 4.8 g (0.022 mol) of 5-acetamino-2-chloro-4-fluoro-thiophenol, 2.55 g (0.064 mol) of sodium hydroxide and 25.5 cc of water were added and stirred under reflux for 4 hours to obtain a uniform solution. The solution was cooled to room temperature and neutralized with 10% hydrochloric acid. The precipitated solid was extracted with 25 cc of ethyl acetate, followed by removal of water and distillation under reduced pressure to obtain 3.8 g of 5-amino-2-chloro-4-fluoro-thiophenol as slightly yellow crystals. Yield was 97.9%.

Physical property: melting point of 64.5°–66.0° C.
Confirmation data: H-NMR(CDCl$_3$) 3.42(2H,s), 3.70(1H,s), 6.68(1H,d,J=8 Hz), 6.97(1H,d,J=10 Hz)

We claim:
1. A bis-(5-acetoamino-2-chloro-4-fluorobenzene)disulfide compound represented by the formula (1):

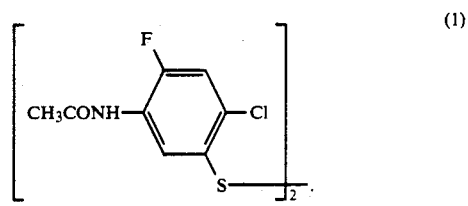

* * * * *